United States Patent [19]

Rosenberg

[11] Patent Number: 4,530,784

[45] Date of Patent: Jul. 23, 1985

[54] LARGE SCALE EXTRACTION PROCESS FOR CONTACT INHIBITORY FACTOR

[75] Inventor: Martin J. Rosenberg, Brooklyn, N.Y.

[73] Assignee: New York University, New York, N.Y.

[21] Appl. No.: 524,917

[22] Filed: Aug. 19, 1983

[51] Int. Cl.³ .............................................. A61K 35/00
[52] U.S. Cl. .................................. 260/112 R; 435/68; 435/41; 435/240; 424/123; 424/124; 424/115
[58] Field of Search ............. 260/112 R; 435/68, 240, 435/41; 424/123, 124, 115, 177

[56] References Cited

U.S. PATENT DOCUMENTS 4,307,082  12/1981  Rosenberg ........................... 435/41

OTHER PUBLICATIONS

Introduction to Modern Biochemistry, 3rd ed., P. Karlson.
Chem. Abstract #11610x, (vol. 81, 1974), Lipkin et al., Diffusible Factor Restoring Contact Inhibition of Growth to Malignant Melanocytes.

Primary Examiner—John Kight
Assistant Examiner—Garnette D. Draper
Attorney, Agent, or Firm—Darby & Darby

[57] ABSTRACT

A method for extracting large quantities of an active biological factor that restores contact inhibition of growth to malignant cell types of different mammalian species.

14 Claims, No Drawings

LARGE SCALE EXTRACTION PROCESS FOR CONTACT INHIBITORY FACTOR

This invention pertains to a method for extracting large quantities of a contact inhibitory factor from a culture medium of contact inhibited cells.

Assignees U.S. Pat. No. 4,307,082 discloses a method for the extraction of a factor that mediates contact inhibition of cell growth. The factor has the ability to restore contact inhibition of growth to non-contact inhibited (malignant) mammalian cells. The factor, denominated contact inhibitory factor (or CIF), has in the past been isolated in crude form from biologically active fractions obtained from 48-72 hour-old, serum-free conditioned culture medium of a contact inhibited hamster amelanotic melanoma cell line. In this instance, the active fraction was separated from the serum-free conditioned media by molecular sieving on a Sephadex G-200 column (available from Pharmacia Fine Chemicals AB, Piscataway, N.J. This technique was reported in an article in the Proceedings of the National Academy of Science, U.S.A., Volume 71, Number 3, pp. 849-853 in March 1974 by Lipkin et al.

More recently, U.S. Pat. No. 4,307,082 of Rosenberg disclosed a method for isolation of contact inhibitory factor by sequentially eluting a fractionating column comprising a non-ionic hydrophobic affinity material with buffers of decreasing ionic strength. Although the hydrophobic interaction separation of Rosenberg yields a more highly purified contact inhibitory fraction (exhibiting a substantially enhanced specific activity) both this procedure and the prior art molecular sieving process produce relatively small quantities of CIF. Thus, using the hydrophobic interaction separation, six liters of starting material (serum-free conditioned media prepared as disclosed in U.S Pat. No. 4,307,082) will yield approximately 0.1 milligrams ($1\times10^{-4}$ grams) of contact inhibitory factor. The relatively low yield of the available procedures for extracting CIF makes it difficult to obtain a sufficient quantity of this material for treatment of mammals and humans, or to serve as a pool for further purification.

A further drawback of the existing CIF isolation processes is that they are relatively complex and expensive to operate. The existing processes generally involve sophisticated column chromatographic techniques. The column packing materials are costly and have limited useful lives. Furthermore, separation of CIF using such column techniques requires a relatively long time period. For example, the hydrophobic interaction chromatography technique disclosed in U.S. Pat. No. 4,307,082 requires approximately nine days between the first and last separation steps.

In view of the acknowledged value of CIF, the art has sought an inexpensive, relatively rapid technique for isolating relatively large quantities of this material.

It has now been discovered that relatively large quantities of CIF can be extracted from serum-free conditioned media without the use of column chromatographic processes. Although the CIF obtained via the non-columnar technique does not have the same high degree of purity as the chromatographic isolate, it can be collected relatively quickly in substantially larger quantities and at minimum costs, thereby making it possible to obtain relatively large quantities of CIF materials that may be used for further purification or for administration to mammals.

According to the present invention, a biologically active factor that restores contact inhibition of growth to malignant cell types in mammals may be extracted by mixing a media conditioned by growth of a contact inhibited cell culture together with a volatile non-denaturing precipitating agent. The precipitate formed by this reaction is separated from the mixture and extracted with a biologically acceptable ionic buffering agent. CIF activity is found in the supernatant extract.

A contact inhibited cell line has been used to produce the extract containing CIF. The cell line employed to illustrate the present invention arose during pigment transformation of a highly malignant, hamster amelanotic melanoma cell line (Roswell Park Memorial Institute, Number 1846; ATCC-CCL-49) by nucleic acids derived by 7,12 dimethyl benz(a)anthrecene (DMBA)-induced, benign, highly pigmented blue nevi of Syrian hamsters. In practice, highly pigmented benign blue nevi tumors are induced in Syrian hamsters by topical application of a single dose of DMBA. The benign tumor corresponds histologically to cellular blue nevi of humans. To obtain nucleic acids for incubations, 110 twelve-week old female Syrian hamsters were painted with 1% DMBA and observed for 8-12 months until maximum blue nevus formation occurred in each animal. At such times, all palpable nevi were carefully excised, trimmed of overlying skin and underlying subutaneous fat, and frozen at $-70°$ C. until ready for use. When sufficient material had been collected, the frozen, pooled, nevi were used as a source of nucleic acids, the latter being extracted with the phenol method. Because of the small quantities of material available, the pooled RNA and DNA obtained was not further separated but used as a mixture in the ratio of 10:1 (RNA:DNA) in incubation.

Prior to use, the pooled nucleic acids were stored for up to six months at $-20°$ C. The purity and concentration of RNA and DNA was determined by employing UV Spectroscopy and Orcinol and Indole assays. Using conventional tissue culture and extraction procedures, the pooled nucleic acids from the benign melanotic (pigmented) nevi cells were added to tissue cultures of amelanotic (RPMI No. 1846) malignant melanoma cells. As a result of this operation, a new cell line (maintained as ATCC No. CRL 1479) was derived from the hamster amelanotic malignant melanoma line (RPMI 1846). Details of the transformation are described in an article by Lipkin in *Journal of Investigative Dermatology*, Volume 57, pages 49-65 (1971).

The new cell line contains amelanotic cells with stable, hereditary properties that differ from those of the parental malignant (RPMI 1846) precursor cell line. The new cell line is available from the American-Type Culture Collection as ATCC CRL-1479. Although aneuploid, the amelanotic (non-pigmented) transformants had the property of density dependent inhibition of cell division and show such features of increased contact inhibition as growth in monolayers of parallel oriented cells, decreased maximum plate density and increased adherence to the culture plate.

To obtain starting materials for practice of the present invention, cultures of cell line ATCC CRL-1479 were initiated and maintained in Falcon T60 Plastic Flasks (No. 3024, Falcon Plastics, Los Angeles, Calif.) on Roswell Park Memorial Institute Medium 1640 (Grand Island Biological Company, Grand Island, N.Y.; formulation identified in Table III U.S. Pat. No. 4,307,082) containing 10% fetal calf serum and antibiotics (1000 units per milliliter of penicillin; 1000 micrograms per milliliter of streptomycin; 2.5 micrograms per milliliter of Fungizone and 600 micrograms per milliliter of Tylocine). Stock cultures are re-fed twice each week and sub-cultured at one to two week intervals.

Tissue cultures of contact inhibited cell line (ATCC CRL-1479) are grown in RPMI 1640 medium containing 10% fetal calf serum and antibiotics until they achieve confluence. The growth medium is then replaced with serum-free RPMI 1640 and the cells maintained for 48 hours to condition the medium by cell growth. After 48 hours, the serum-free conditioned medium is centrifuged for approximately five minutes at 1500 rpm to remove detached cells. The supernatant recovered from the centrifuge is the starting material for the present invention.

100 milliliters of the serum-free conditioned medium (supernatant recovered from the centrifuge) is placed in a 500 milliliter Ehrlenmeyer flask. The flask is chilled in the refrigerator for about one hour until the contents reach a temperature of about 4°–12° C., preferably 4° C. The flask is removed from the refrigerator and placed on a magnetic stirrer. The orifice of a buret containing a volatile non-denaturing precipitating agent is located directly above the mouth of the Ehrlenmeyer flask. The precipitating agent is at the same temperature as the serum-free conditioned media held in the Ehrlenmeyer flask.

The volatile non-denaturing precipitating agents found to be useful in the present invention include C1 to C3 alkylalcohols (e.g. methyl, ethyl, and propyl alcohols), acetonitrile and ethyl acetate. This list of materials is not all-inclusive and is merely exemplary. Virtually any material that is volatile (has a boiling point below the boiling temperature of water) and non-denaturing (i.e. does not denature protein) may be used as the precipitating agent in the present process.

The precipitating agent is dispensed drop-wise from the buret into the serum-free conditioned medium. Throughout the addition of the precipitating agent, the mixture is constantly stirred by operation of the magnetic stirring apparatus. The entire operation is conducted in a cold room to maintain the temperature of the reaction mixture at between 4°–12° C., but preferably at 4° C. A sufficient quantity of precipitating agent is dispensed into the serum-free conditioned medium to create a ratio of serum-free conditioned medium to precipitating agent (by volume) of between 60:40 to 40:60. Preferably, a mixture comprising equal volumes of serum-free conditioned medium and precipitating agent (50:50 ratio) is employed in the present process. The mixture is stirred for between 4–16 hours during which time a flocculent white precipitate is formed.

The reaction mixture is transferred to a Sorval RC2-B refrigerated super-speed centrifuge (Sorvall Manufacturing Company, Norwalk, Conn.). The centrifuge is run at 10,000 rpm for 10 minutes at 4° C. After decanting the supernatant, the entire centrifuge tube is placed in a large lyophilization flask and the precipitate lyophilized overnight. The lyophilized precipitate weighed 50 mg.

The lyophilized precipitate in the centrifuge tube was extracted in two successive extractions with a biologically acceptable ionic buffer. A total of 5 ml of buffer was employed to perform the extractions (3 ml of buffer in the first extraction, 2 ml of buffer solution used in the second extraction). Suitable buffers for use in the present invention include phosphate buffered saline solutions of the formula described in Table I below.

| Phosphate Buffered Saline Solution: | |
| --- | --- |
| NaCl | 0.14 M |
| KCL | 0.003 M |
| Na$_2$HPO$_4$ | 0.15 M |
| KH$_2$PO$_4$ | 0.15 M |
| | pH = 7.2 |

Although the phosphate buffered saline solution of Table I is preferred for use in the present invention, the process may be operated with any biologically acceptable ionic buffer including, for example, Tris, Hepes, and sodium bicarbonate. Preferably, the ionic buffer solutions of the present invention should fall without the range pH 6.5–7.5 preferably pH 7.2.

Three ml of the ionic buffer of Table I are added to the centrifuge tube and the tube transferred to a Vortex Mixer (Fisher Scientific Supply Company, Princeton, N.J.) and agitated until the precipitate is in suspension, usually between 10–15 seconds. The tube is then transferred to an ultrasonically agitated bath (Ultrasonics Inc., Brooklyn, N.Y.). Crushed ice is added to the ultrasonic bath solution to prevent overheating. The test tube is allowed to remain in the ultrasonic bath for a period of approximately one hour during which time the ultrasonic device is operated. Ultrasonic treatment reduces the particle size of the precipitate thereby increasing the surface area exposed to the ionic extractant. This in turn reduces the amount of time required to effect an efficient extraction.

After one hour the centrifuge tube is removed from the ultrasonic bath, replaced in the Sorvall Centrifuge and spun at 10,000 rpm at 4° C. for 10 minutes. The supernatant is carefully removed from the centrifuge tube, placed in a sterile 10 milliliter test tube and stored in a refrigerator at 4° C. Two milliliters of fresh ionic buffer is added to the residual precipitate remaining in the centrifuge tube and the previous extraction procedure (vortex mixing, ultrasonication, and centrifugation) repeated under the same conditions described above. The resulting supernatant fluid is carefully removed from the centrifuge tube and added to the test tube containing the material of the first extraction. The test tube containing the total amount recovered (5 milliliters of fluid) is stored in the refrigerator at 4° C. for further use.

To confirm that the fluid in the test tube contains CIF, the following test was performed. One milliliter of the CIF extract contained in the refrigerated test tube is added to 3 milliliters of the liquid growth medium (RPMI No. 1640, 10% fetal calf serum, and antibiotics; 1000 units per milliliter of penicillin, 1000 micrograms per milliliter of streptomycin, 2.5 micrograms per milliliter of Fungizone and 600 micrograms per milliliter of Tylocine). The growth inhibitory properties of the extract were tested against subconfluent cell cultures of amelanotic malignant melanoma cells (RPMI No. 1846 also maintained as ATCC CCL 49). These cells are hereinafter referred to as AM cells. The AM cells are suspended in the complete growth medium prepared above, and pipetted into Falcon Microtest III Tissue Culture Plates, 96 wells (Falcon Plastics, Los Angeles, Calif.) at a concentration of 10,000 cells per well. The plate containing the wells is incubated at 37° C. for 2 hours, to permit the cells to become adherent to the bottom of well. At the end of the two hour period, the supernatant is removed from the microtest well and 0.2 of a milliliter of the previously prepared growth medium containing CIF extract added to each well of the microtest plate. The microtest plate is returned to the incubator and held at 37° C. under an atmosphere containing 5% carbon dioxide. The plates are observed daily and fed at two day intervals. Control wells on each plate contain the same types of cell and growth medium, but do not contain the CIF extract obtained through the present invention. The cell densities and percent inhibition of growth of AM hamster melanoma cell cultures with the CIF-containing extract obtained according to the present invention is illustrated in Table II.

TABLE II

| No. of Days after Plating | CIF Extract Mcg./ml of Protein | cells/ well | % inhibition of growth |
|---|---|---|---|
| 3 | 0 (control) | 43 × 10⁴ | 0 |
| 3 | 220 | 8.5 × 10⁴ | 80% |
| 5 | 0 (control) | 51 × 10⁴ | 0 |
| 5 | 220 | 10.7 × 10⁴ | 79% |

Referring to Table II, it can be seen that inhibition of cell growth was obtained using the CIF containing extracts of the present invention. Observation of the test specimens reveal that AM malignant melanoma cells grown on test media containing the CIF extract of the present invention have undergone morphological changes. Although the test wells originally contained an overgrowth of disoriented, pleomorphic cells, after incubation the wells held monolayers of well oriented cells that adhered to the underlying substrate. The growth inhibitory affects and morphological changes were consistent with the growth inhibitory effects on those cells cultured in media containing CIF. Those cultures were generally less crowded and the cells tended to remain in adherent monolayers instead of being detaching or forming irregular clusters or piles. The CIF treated cultures also show substantial decreases in saturation density without loss of cell viability.

What is claimed is:

1. A method for obtaining a biologically active factor that restores contact inhibition of growth to malignant cell types, from media conditioned by growth therein of a contact-inhibited cell culture, which comprises
mixing said media with a volatile non-denaturing precipitating agent to form a precipitate,
separating said precipitate from said mixture,
extracting said precipitate with a biologically acceptable ionic buffer,
agitating said precipitate and said buffer,
centrifuging the buffer and precipitate, and
collecting the supernatant buffer from said centrifuging operation and recovering said factor from said buffer, said factor being obtained in substantially higher quantity and yield than that resulting from use of hydrophobic interaction chromatography for isolating said factor from said media.

2. The method of claim 1 which comprises mixing said precipitating agent with said media at a temperature between about 4° C. and about 12° C.

3. The method of claim 2 wherein said precipitating agent is a member selected from the group consisting of $C_1$-$C_3$ alcohols.

4. The method of claim 2 wherein said precipitating agent is acetonitrile.

5. The method of claim 2 wherein said biologically acceptable buffer is ethyl acetate.

6. The method of claim 2 which comprises maintaining said precipitating agent and said media at the same temperature during said mixing step.

7. The method of claim 2 which comprises adding a sufficient quanitity of said precipitating agent to said media to create a ratio of said serum-free conditioned medium to said precipitating agent of between about 60:40 to about 40:60 by volume.

8. The method of claim 3 which comprises subjecting said precipitate to two separate sequential extracting with said ionic buffer.

9. The method of claim 8 wherein said ionic buffer is a phosphate buffered saline solution.

10. The method of claim 8 wherein the pH of said ionic buffer solution is between about pH 6.5 and pH 7.5.

11. The method of claim 8 wherein said ionic buffer solution comprises Hepes.

12. The method of claim 8 wherein said ionic buffer solution comprises sodium bicarbonate.

13. The method of claim 8 which comprises agitating said ionic buffer and said precipitate during said extracting step.

14. The method of claim 13 which comprises agitating said ionic buffer and said precipitate at ultrasonic frequencies.

* * * * *